(12) United States Patent
Jamiolkowski et al.

(10) Patent No.: US 6,514,517 B2
(45) Date of Patent: Feb. 4, 2003

(54) ANTIMICROBIAL COATINGS FOR MEDICAL DEVICES

(75) Inventors: Dennis D. Jamiolkowski, Long Valley, NJ (US); Stephen Jude Rothenburger, Phillipsburg, NJ (US); Daniel J. Spangler, Whitehouse Station, NJ (US)

(73) Assignee: Ethicon, Inc., Somerville, NJ (US)

( * ) Notice: Subject to any disclaimer, the term of this patent is extended or adjusted under 35 U.S.C. 154(b) by 7 days.

(21) Appl. No.: 09/885,714

(22) Filed: Jun. 20, 2001

(65) Prior Publication Data

US 2002/0197185 A1 Dec. 26, 2002

(51) Int. Cl.[7] .............................. A61F 2/02; A61K 47/30; A61K 47/32

(52) U.S. Cl. ................. 424/426; 514/772.3; 514/772.5; 514/772.6

(58) Field of Search ................................. 424/423, 424, 424/425, 426; 514/772.3, 772.5, 772.6

(56) References Cited

U.S. PATENT DOCUMENTS

| 5,877,243 A | 3/1999 | Sarangapani |
| 6,126,931 A | 10/2000 | Sawan et al. ............ 424/78.09 |

*Primary Examiner*—Carlos Azpuru

(57) ABSTRACT

The present invention is directed to compositions containing an acid precursor in amounts effective to inhibit microbial attachment and growth on a surface of a medical device having the composition applied thereto, to films of such compositions and to medical devices having the composition applied to a surface thereof.

15 Claims, 1 Drawing Sheet

ANTIMICROBIAL COATINGS FOR MEDICAL DEVICES

FIELD OF THE INVENTION

The present invention relates to biocompatible, antimicrobial compositions that are useful as coatings on medical devices to inhibit attachment and/or growth of microorganisms on the medical device.

BACKGROUND OF THE INVENTION

Postoperative surgical site infections (SSIs) occur in approximately 2.5% of all patients who undergo surgical procedures. In essentially all cases, some type of medical device is utilized by the surgeon and remains in the patient following surgery. The type of medical device implanted in the human body varies depending on the nature of the operation. It is quite common that some type of suture or other wound closure material or device is utilized. While the body's immune response normally is successful in preventing microbial infection at the wound site, in the presence of foreign matter, such as the medical device, the probability of infection increases significantly.

Most infections associated with medical device implantation are caused by bacteria. Coagulase negative Staphylococcus species are the primary cause of these infections, accounting for 30–40% of all SSIs. Staphylococcus aureus is involved in 10–20%, Streptococcus species cause 5–10%, and Enterococcus species account for another 10–15%. It is obvious that Gram positive bacteria are the causative infectuous agents in the majority of SSIs relative to medical device implantation. Gram negative bacteria Pseudomonas, E. coli, Enterobacter, and other coliforms) account for 10–20% of these infections, and the remainder are due to yeasts, fungi and anaerobic bacteria.

The primary mode of infection associated with medical device implantation is attachment of microorganisms, e.g. bacteria, to the device, followed by growth and formation of a biofilm on the device. Subsequent release and migration of the microbial contaminant from the biofilm to tissue immediate to and surrounding the device results in a SSI. Once a biofilm is present on a medical device, it is practically impossible to treat the infection without actually removing and replacing the device.

While antimicrobial substances or toxins, i.e. substances which in and of themselves are toxic to microorganisms capable of causing infection at surgical sites, may be added to medical devices, they typically have limitations. Many of the antimicrobial substances are toxic to the patient, while others cause allergic reactions. In addition, certain microorganisms are resistant to such antimicrobial substances due to the development of defense mechanisms that actually destroy the antimicrobial molecule. For example, Penicillinase is produced by Staphylococcus species to break down penicillin.

Oxidized regenerated cellulose (ORC) hemostatic agents have been shown to have broad-spectrum antimicrobial activity due to their pH lowering properties. A general discussion of the in-vitro and in-vivo antimicrobial properties of ORC is found in Dineen, P., "Antibacterial Activity of Oxidized Regenerated Cellulose", SURGERY, Gynecology and Obstetrics, April 1976, Volume 142, number 4. In a related article found in Dineen, P., "The Effect of Oxidized Regenerated Cellulose on Experimental Intravascular Infection", SURGERY, November 1977, Volume 82, number 5, it is stated that the mechanism of action of ORC apparently is mediated through its pH effect, because in vitro the antibacterial action can be reduced or eliminated by the use of sodium hydroxide.

In certain coatings used to provide medical devices with bacteria-resistant surfaces, acid-chelating components are reactively bound to a hydrophilic polyurethane prepolymer along with noble metal combinations or antibacterials. It is noted that such noble metals and/or antibacterials are necessary in order for such coatings to provide such antimicrobial effect.

It is important to note that in the example presented above, when ORC is placed in the body, the pH effect is very localized and controlled and results in no adverse effect on the tissue in the immediate or surrounding environments.

In order to provide safe and efficient prevention of infections related to the implantation of medical devices, it would be advantageous to provide an implantable device capable of inhibiting the attachment and/or growth of microorganisms thereto. In order for a medical device to effectively resist microbial attachment and subsequent growth, it must possess an antimicrobial property that is broad spectrum, i.e. it is effective in inhibiting the attachment and/or growth of a large spectrum of microorganisms capable of causing infection.

We unexpectedly have discovered a means to provide such antimicrobial properties to a wide variety of implantable devices through the use of a biocompatible, antimicrobial coating applied to the device. Advantageously, the antimicrobial property can be imparted to the device without significant cost increase or significant alteration of the mechanical properties of the device.

SUMMARY OF THE INVENTION

The present invention is directed to compositions containing a biocompatible acid precursor in amounts effective to inhibit microbial attachment and/or growth on a surface of a medical device having the composition applied thereto, to coatings or films prepared from such compositions and to medical devices having the composition applied to a surface thereof Once the coated medical device is placed in the body of a mammal, e.g. a human or animal, the acid precursor in the coating produces acid moieties at concentrations effective to maintain the pH of the coating and/or the tissue area immediate to and adjacent the device at a level effective to inhibit microbial attachment and/or growth on the coated surface of the medical device. The acid precursor may diffuse through the coating and then hydrolyze at the surface of the coated device, or in the immediate vicinity. Alternately, or in combination with the above, upon implantation of the coated device, the acid precursor may first hydrolyze, with the resulting acid diffusing through the coating to the surface to provide the effective pH.

DETAILED DESCRIPTION OF THE INVENTION

Microorganisms have certain general requirements for survival and growth, including an appropriate temperature range, nutrients, oxygen, moisture and pH. If any of these basic requirements are not met, the microorganism will not grow, and if growth does not occur, microorganisms in general will not survive. Extremes in acidity or alkalinity can effectively limit growth and survival of microorganisms, including Staphylococci, Pseudomonas, Streptococci, Coliforms, and others commonly associated with medical device-related SSIs.

In the body of mammals, e.g. humans and animals, microorganisms will encounter nutrients, temperature, moisture and oxygen required for growth. In most cases, the pH also will be in a range generally acceptable for growth. However, there are areas of the body where a naturally occurring low pH enables the body to resist infection. Lactobacillus species colonize the vagina, producing lactic acid, which lowers the pH, producing an inhospitable habitat for numerous other microorganisms, including pathogens. In the sebaceous glands associated with hair follicles, fatty acids and lactic acid are produced, which lower the pH and inhibit the growth of pathogenic bacteria. Populations of microorganisms in the stomach usually are transient and their populations are kept low by acidity.

One aspect of the present invention involves the modification of the surface of a medical device by applying thereto a coating or film comprising a composition that contains a biocompatible acid precursor capable of generating acid-moieties in or about the coating or film. The acid precursor is present in amounts effective to provide the surface of the device with a coating or film having a pH effective to inhibit attachment and/or growth of microorganisms on the surface of the device. The coating does not require conventional antimicrobial agents, such as noble metals or antibacterials, in addition to the acid precursor to provide antimicrobial properties. The pH of the coating will be below the pH at which attachment and/or growth of microorganisms on the surface of the device is sustained. Microorganisms may otherwise be referred to herein as microbes. The effective pH conditions are produced upon implantation of the device in the body and persist for a period of time thereafter such that the coating inhibits or prevents microbial attachment and/or growth on the device. In certain instances, the low, effective pH conditions may persist for a matter of hours or days.

Figure 2:
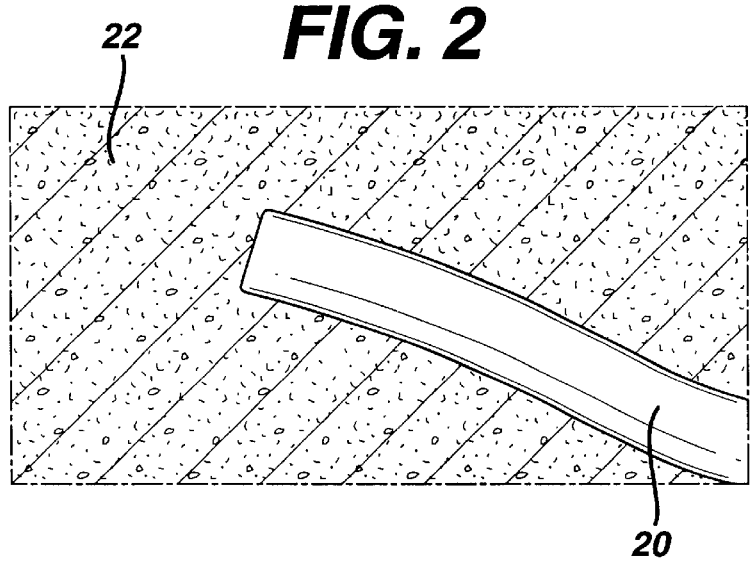
FIG. 2 is a top view of a conventional suture.
Figure 3:
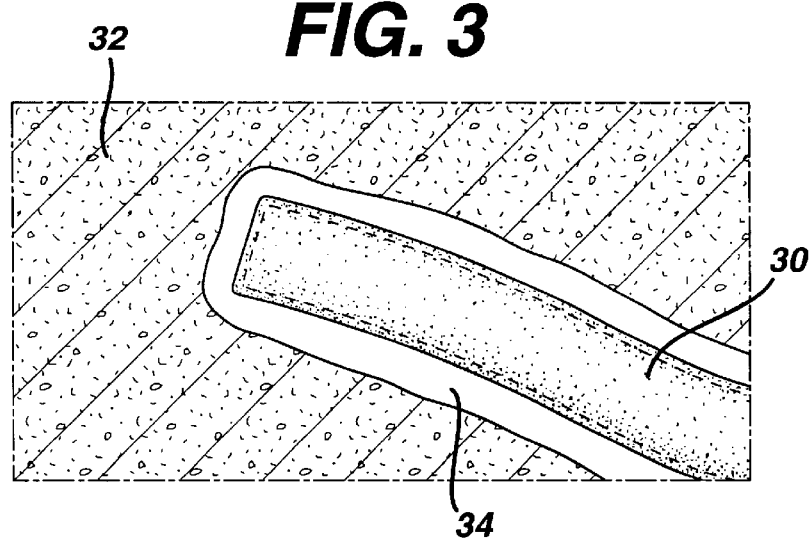
FIG. 3 is a top view of a suture of the present invention.

The coated device thus possesses antimicrobial properties required to inhibit attachment and/or growth of the microorganism on the device, without the presence of conventional antimicrobial agents, such as noble metals or antibacterials. In addition, the presence of the coating on the device may serve to inhibit growth of microorganisms in tissue either in contact with or in the immediate vicinity of the coated device. As noted in FIG. 2, in a conventional device, e.g. suture 20, containing no antimicrobial coating according to the present invention, microorganisms 22 noticeably are present growing in the area immediate to and adjacent the uncoated suture. Such an environment is conducive to attachment and growth of microorganisms not only in the surrounding area, but also to the surface of the device. However, as shown in FIG. 3, a coated device according to the present invention, e.g. coated suture 30, exhibits a zone of inhibition 34 immediately surrounding the suture, where the substantial absence of growth of microorganisms 32 in the area immediate to and adjacent the coated suture clearly is noted.

It should be noted that in order for devices of the present invention to possess antimicrobial properties, it is not necessary for an eluting antimicrobial substance to be produced by the device to seek and destroy microorganisms in the surrounding environment. Since infection also can be the result of non-aseptic surgical technique and the presence of antibiotic resistant microorganisms introduced into the wound site during surgery, the coating can not be expected to compensate for such factors. However, since attachment and growth on the device is the primary mode of infection, inhibition of this sequence represents a significant antimicrobial advantage.

According to one aspect of the present invention, medical devices having antimicrobial properties, e.g. antimicrobial sutures and meshes, may be prepared by coating the devices with compositions containing hydrolyzable lactones in amounts effective to provide coatings capable of inhibiting attachment and/or growth of microorganisms thereon. The compositions may comprise from about 0.1 to about 100 weight percent of hydrolyzable lactone, based on total weight of the coating composition. Typically, the compositions may comprise from about 10 to about 30 weight percent hydrolyzable lactone monomer, and more preferably about 20 percent by weight of the hydrolyzable lactone monomer, based on total weight of the coating composition The coated devices may comprise from about 0.1 to about 20 percent by weight of the coating composition, based on the total weight of the coated device. Preferably, when the device is a surgical suture or mesh, it may comprise from about 1 to about 10 weight percent of the coating composition, more preferably from about 2 to about 5 weight percent, based on total weight of the coated device. The coated device may comprise from 0.001 to about 20 weight percent of the hydrolyzable acid precursor, based on total weight of the coated device. When the medical or surgical device is metallic in nature, e.g. a suture anchor, the relative amount of coating required to provide the antimicrobial properties, on a weight percent basis, will be lower than if the device is polymeric in nature. As the surface area of the device is lower, the relative amount of coating, on a weight basis, also will be lower. Thus, a coated suture may comprise about 3 percent by weight of coating, while a metallic suture anchor may comprise only about 0.5 percent by weight of coating. Regarding sutures, as the diameter of the suture increases, e.g. size 6/0 to size 2/0, the relative amount of coating required also will be lower.

Figure 1:
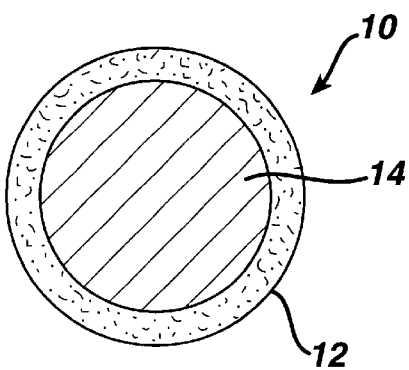
FIG. 1 is a cross-sectional view of a suture of the present invention.

Referring to FIG. 1, a cross-section view of cylindrical-shaped medical device according to the present invention, e.g. coated suture 10, is shown. Suture 14 has applied thereto an effective amount of coating 12 comprising hydrolyzable acid precursors, which will produce pH-lowering acid moieties upon hydrolysis, thereby producing an antimicrobial effect.

In addition to sutures shown herein, devices according to the present invention include, without limitation, surgical mesh, catheters, stents, prosthetic joints and limbs, bone implants and anastomotic devices. While medical devices may be in the form of surgical sutures or meshes produced from known polymeric suture and mesh materials, alternately, the medical devices may be metallic in nature.

The medical-device coatings of the present invention may comprise effective amounts of acid precursors selected from the group consisting of hydrolyzable cyclic esters (i.e. hydrolyzable lactones), acylic esters having number average molecular weights of 800 or less and in which the acid-based moiety comprises a heteroatom adjacent to the α-carbon, cyclic anhydrides of 5, 6 or 7 atoms, and mixed or symmetrical linear anhydrides of carboxylic acids of 24 or less carbons, each of which is capable of providing antimicrobial properties to the substrates onto which they are coated when placed in the body of humans or animals.

Hydrolyzable cyclic esters that may be used according to the present invention include, without limitation, hydrolyzable lactones, especially those comprising 5, 6, or 7 member rings. Preferred cyclic esters include glycolide, L(−)-lactide, D(+)-lactide, mesolactide, p-dioxanone and glucono-δ-lactone. Other acid precursors within the scope of the invention include molecules that contain as part of their chemical structure hydrolyzable cyclic ester moieties.

Linear esters that may be used according to the present invention include those having number average molecular weight of about 800 or less and in which a majority of the acid moieties comprise a heteroatom next to the α-carbon. Oxygen is one preferred heteroatom. Such preferred acid-moieties include, without limitation, hydroxyalkyloxyacetic acid (i.e. β-hydroxyethoxyacetic acid), glycolic acid and lactic acid. Preferred linear esters include oligo(ethylene 3,6-dioxaoctanedioate), oligo(ethylene 3,6,9-trioxaundecanedioate) and oligo(glycolide-co-lactide), each having a number average molecular weight of about 800 or less.

Cyclic Anhydrides comprising 5, 6 or 7 member rings that may be used according to the present invention include, without limitation, succinic anhydride, maleic anhydride, diglycolic anhydride and glutaric anhydride.

While linear anhydrides of carboxylic acids comprising about 24 or less carbon atoms may be used, those comprising a lower number of carbon atoms generally are preferred, as they hydrolyze faster. Examples include, without limitation, formic, acetic, propionic and buteric anhydrides. The actual preferred number of carbon atoms will depend on the device, the presence or absence of a polymeric coating and its characteristics. However, when linear anhydrides that comprise acid moieties comprising a heteroatom next to the α-carbon are utilized, anhydrides comprising a higher number of carbon atoms, e.g. 6 to about 24 carbon atoms, are preferred. Oxygen is a preferred heteroatom Examples of such acid-moieties include the family of hydroxyalkyloxy-acetic acids (i.e. β-hydroxyethoxyacetic acid). In addition, mixed anhydrides based on, for example, 3,6,9-trioxaundecanedioic acid and, for instance, acetic acid, are possible.

In preferred embodiments of the invention, lactones, including lactide and glycolide, alone or in combination, are present in the coating at a relative ratio and total concentration that will provide the coating with a rate of release and concentration of lactic and/or glycolic acid upon hydrolysis of the ester in the human body that will be effective to provide the surface of the coated device the pH necessary to inhibit attachment and/or growth thereon. Alternately, or in combination with the cyclic esters, acylic esters such as glycyl glycolate, lactyl lactate, lactyl glycolate and oligo (lactide-co-glycolide), each having a number average molecular weight of about 800 or less, can be employed. The specific relative ratio and total concentration of lactones or of the oligo(lactide-co-glycolide) in the coatings will depend in part on the nature of the device to be coated and the particular use of the device in the body. Lactic and/or glycolic acid will be produced at concentrations capable of inhibiting microbial attachment and/or growth on the coated device and that will be sufficient to overcome the buffering capacity of the body tissues and fluids contacting the device. The concentration and ratio of the lactones and the oligo (lactide-co-glycolide) added to the coatings are adjusted so that the concentration of acid produced does not reach a level where surrounding tissue will be adversely affected.

In a further aspect of the invention, the coating composition may further comprise a component to modify the release rate of the acid precursor or of the hydrolyzed acid precursor (i.e. carboxylic acid) in order to extend the antimicrobial action. Such components may include polymeric-based compositions, for example poly(ethylene 3,6,9-trioxaundecanedioate) or poly(caprolactone-co-glycolide).

In selecting a particular acid precursor for use in coating a particular device, one considers, in part, the release characteristic of the acid precursor or the acid derived therefrom, i.e. the ability to diffuse through the coating and the rate of diffusion to the surface. In addition, the ability of an acid precursor to hydrolyze at a rate effective for use in such coatings that provide an antimicrobial effect is considered in selecting an acid precursor. For example, if the molecular weight of the acid precursor is too high, the precursor may not hydrolyze readily upon implantation into the body. Also considered in the case of coatings for multifilament suture materials will be the lubriciousness of the coating prepared from the acid precursor. One skilled in the art, once having the benefit of this disclosure, will be able to determine particular acid precursors and effective levels thereof for preparation of coatings and devices according to the present invention.

The following examples are provided to further describe certain embodiments of the invention but are in no way limiting to the scope of invention.

EXAMPLE 1

We have discovered unexpectedly that when effective amounts of hydrolyzable lactones, such as glycolide or lactide, were placed on agar plates seeded with Gram positive and Gram negative bacteria, large zones of inhibition were noted in a modified Kirby Bauer test as described below. Samples of glycolide and L(−)-lactide were placed in plastic pouches, sealed, and subjected to cobalt irradiation at a dose of 2.5–3.3 Mrad in order to sterilize the preparations. Non-sterile lactide and glycolide were utilized as controls. Both the sterilized and non-sterilized glycolide and lactide samples were placed on separate Mueller-Hinton agar plates that had been heavily seeded using a sterile swab with 24 hour cultures of *Staphylococcus aureus, Staphylococcus epidermidis, Pseudomonas aeruginoa*, and *Escherichia coli*. Plates were incubated upright (lid side up) at 30–35° C. for 24 hours. Upon examination, it was noted that plates comprising monomer on the surface thereof, including both the sterilized and non-sterilized monomers, were surrounded by zones of inhibition extending from about 40 mm–70 mm therefrom. By zone of inhibition, it is meant that area immediate or adjacent to the coating, or coated device, in this instance the coated agar plates, where growth of bacteria is inhibited by the effects of the coating, i.e. a pH is provided that is effective to inhibit growth of bacteria in an area immediate or adjacent to the coated device.

While the following scientific theory is in no way intended to limit the scope of the invention, it is believed that the glycolide and lactide monomers hydrolyze to glycyl glycolate and lactyl lactate, respectively. These species are carboxylic acids that can lower pH locally. These materials can undergo further hydrolysis to glycolic acid and lactic acid, respectively. The acid precursor may diffuse through the coating to hydrolyze at the surface of the device or, upon implantation, may hydrolyze first, followed by diffusion of the resulting acid to the surface of the coated device.

EXAMPLE 2

In order to further evaluate the in-vitro potential for pH-lowering coatings, a study was carried out with *Staphylococcus aureus* ATCC33591. A series of coatings was prepared by dissolving 2.5, 5, 10 and 20 percent (w/w) of L(–)-lactide, respectively, in ethyl acetate. A second series of coatings was prepared by dissolving 2.5, 5, 10 and 20 percent (w/w) of L(–)-lactide in combination with 9 percent (w/w) polyoxaester, respectively, in ethyl acetate.

The polyoxaester coating copolymer used was a poly (ethylene 3,6,9-trioxaundecanedioate-seg-caprolactone-co-glycolide) resin comprised of approximately 17 weight percent polyoxaester prepolymer and a 83 weight percent polymerized mixture of approximately 91 mole percent ε-caprolactone and 9 mole percent glycolide. The polyoxaester is a polycondensation product of 3,6,9-trioxaundecanedioic acid and ethylene glycol made to have hydroxyl functionalities at both ends of each chain. The final resin is made through a ring opening polymerization of the ε-caprolactone and glycolide mixture using the polyoxaester as an α,ω-dihydroxy-macroinitiator. The inherent viscosity of the coating copolymer was 0.55 dL/g as determined in hexafluoroisopropanol (HFIP) at 25° C. at a concentration of 0.1 g/dL. Gel permeation chromatography (GPC) results indicate a number average molecular weight of 11,000 g/mole with a weight average of 19,000 g/mole.

A third series of coatings was prepared by dissolving 2.5, 5, 10 and 20 percent (w/w) of glycolide, respectively, in ethyl acetate. A fourth series of coatings was prepared by dissolving 2.5, 5, 10 and 20 percent (w/w) of glycolide in combination with 9 percent (w/w) polyoxaester coating copolymer, respectively, in ethyl acetate. Approximately one-inch sections of commercial size 2/0 synthetic absorbable braided [10/90 poly(lactide-co-glycolide)] suture were dipped into the solutions and were dried overnight in a laminar flow hood, thereby providing a coated suture according to the present invention. In a Kirby-Bauer type test, plates were seeded with a 24-hour culture of *Staph. aureus*. The coated suture sections were placed on agar plates and the plates were incubated at 30–35° C. for 24 hours. Upon inspection, it was noted that plates having glycolide and lactide coatings applied thereto, alone or in combination with 9 percent polyoxaester coating copolymer, exhibited zones of inhibition extending from the edge of the device. For sutures coated from solutions comprising 2.5 percent and 5 percent lactide, respectively, zones of inhibition extending approximately 1 mm from the coated suture were observed. Sutures coated from coating solutions comprising 2.5 percent and 5 percent glycolide exhibited zones of inhibition of less than 1 mm. Sutures coated from coating solutions comprising 10 percent lactide or glycolide showed zones of inhibition of approximately 1 mm. Utilizing a 20 percent lactide coating solution, the zone of inhibition was greater than 1 mm. All other coatings yielded results approximately the same as those obtained from a 10 percent lactide coating solution. The presence of 9 percent polyoxaester coating copolymer appeared to neither enhance nor significantly diminish the antimicrobial effect of the lactide and glycolide. As shown by comparison to untreated control sutures, it is clear that the addition of the acid-releasing coatings to the sutures resulted in a significant antimicrobial effect against *Staphylococcus aureus* ATCC 33591.

Referring to FIG. 3, a one inch-section of suture 30 coated with a solution of 20 percent by weight lactide in ethyl acetate was placed on a seeded agar plate and incubated as above. Zone of inhibition 34 clearly surrounds coated suture 30, while microorganisms 32 can be seen growing on the agar plate outside of zone of inhibition 34. Referring to FIG. 2, when a section of untreated suture 20 is placed on a seeded agar plate and incubated as above, microorganisms 22 are present immediate and adjacent to the untreated suture and no zone of inhibition is noted around the suture.

EXAMPLE 3

An alternative formulation designed to enhance the physical durability of the acid-precursor-containing coating was prepared by mixing a polyoxaester coating copolymer (20% by weight) with lactide (18% by weight) and lactic acid (2% by weight), all in ethyl acetate. The total solids in the mix were about 40% by weight. The formulation was coated onto nonabsorbable polypropylene monofilament suture by dipping to about 20–40% by weight of the suture. The coated suture was challenged in a zone of inhibition assay by placing the suture on agar plates seeded with Staphylococcus aureus. The plates were incubated at 30–35° C. for 24 hours, and the zones were measured in millimeters. After ethylene oxide sterilization, the coating yielded zones of inhibition of approximately 7 mm. This compares with untreated suture controls in which the microorganisms are present immediate and adjacent to the suture; i.e. no zone of inhibition for the untreated controls.

We claim:

1. A composition, comprising:
   a hydrolyzable acid precursor in amounts effective to inhibit microbial attachment and/or growth on a surface of a medical device having said composition applied thereto, wherein said acid precursor produces acid moieties at concentrations effective to maintain the pH of said surface at a level effective to inhibit microbial attachment and/or growth on said surface of said medical device.

2. The composition of claim 1 comprising from about 0.1 to about 100 percent by weight of said hydrolyzable acid precursor.

3. The composition of claim 1 comprising from about 10 to about 30 percent by weight of said hydrolyzable acid precursor.

4. The composition of claim 1 comprising about 20 percent by weight of said hydrolyzable acid precursor.

5. The composition of claim 1 wherein said hydrolyzable acid precursor is selected from the group consisting of hydrolyzable cyclic esters having 5, 6 or 7 member rings, linear esters having number average molecular weight of about 800 or less and in which the majority of acid moieties possess a heteroatom next to the α-carbon, cyclic anhydrides comprising 5, 6 or 7 member rings, mixed or symmetrical linear anhydrides of carboxylic acids of 24 or less carbons, and combinations thereof.

6. The composition of claim 1 wherein said hydrolyzable acid precursor is selected from the group consisting of glycolide, L(–)-lactide, D(+)-lactide, meso-lactide, p-dioxanone, glucono-δ-lactone, glycyl glycolate, lactyl lactate, lactyl glycolate, oligo(ethylene 3,6-dioxaoctanedioate), oligo(ethylene 3,6,9-trioxaundecanedioate), oligo(glycolide-co-lactide), succinic anhydride, maleic anhydride, diglycolic anhydride, glutaric anhydride, formic anhydride, acetic anhydride, propionic anhydride and buteric anhydride.

7. A film prepared from the composition according to claim 1.

8. A medical device comprising a film according to claim 7 applied to a surface thereof.

9. A medical device, comprising:
   a composition applied to at least one surface of said device, said composition comprising a hydrolyzable acid precursor in amounts effective to inhibit microbial attachment and/or growth on said surface of said medical device having said composition applied thereto, wherein said acid precursor in said composition produces acid moieties at concentrations effective to maintain the pH of said surface of said device at a level effective to inhibit microbial attachment and/or growth on said surface of said medical device.

10. The device of claim 9 comprising from about 0.1 to about 20.0 percent by weight of said composition.

11. The device of claim 9 comprising from about 2 to about 5 percent by weight of said composition.

12. The device of claim 9 comprising from about 0.001 to about 20 percent by weight of said hydrolyzable acid precursor.

13. The device of claim 9 wherein said hydrolyzable acid precursor is selected from the group consisting of hydrolyzable cyclic esters having 5, 6 or 7 member rings, linear esters having number average molecular weight of about 800 or less and in which the majority of acid moieties possess a heteroatom next to the α-carbon, cyclic anhydrides comprising 5, 6 or 7 member rings, mixed or symmetrical linear anhydrides of carboxylic acids of 24 or less carbons, and combinations thereof.

14. The device of claim 9 wherein said hydrolyzable acid precursor is selected from the group consisting of glycolide, L(−)-lactide, D(+)-lactide, meso-lactide, p-dioxanone, glucono-δ-lactone, glycyl glycolate, lactyl lactate, lactyl glycolate oligo(ethylene 3,6,9-trioxaundecanedioate), oligo(glycolide-co-lactide), succinic anhydride, maleic anhydride, diglycolic anhydride, glutaric anhydride, formic anhydride, acetic anhydride, propionic anhydride and buteric anhydride.

15. The device of claim 10 selected from the group consisting of sutures, mesh, catheters, stents, prosthetic joints and limbs, bone implants and anastomotic devices.

* * * * *